(12) United States Patent
Aldon et al.

(10) Patent No.: US 12,102,807 B2
(45) Date of Patent: Oct. 1, 2024

(54) DOSE CONTROL SYSTEM FOR INJECTABLE-DRUG DELIVERY DEVICES AND ASSOCIATED METHODS OF USE

(71) Applicant: BIOCORP PRODUCTION S.A., Issoire (FR)

(72) Inventors: Lionel Aldon, Chanonat (FR); Alain Marcoz, Montmorin (FR)

(73) Assignee: Biocorp Production S.A.S., Issoire (FR)

(*) Notice: Subject to any disclaimer, the term of this patent is extended or adjusted under 35 U.S.C. 154(b) by 858 days.

(21) Appl. No.: 16/479,782

(22) PCT Filed: Jan. 25, 2017

(86) PCT No.: PCT/IB2017/000306
§ 371 (c)(1),
(2) Date: Jul. 22, 2019

(87) PCT Pub. No.: WO2018/138542
PCT Pub. Date: Aug. 2, 2018

(65) Prior Publication Data
US 2021/0330892 A1    Oct. 28, 2021

(51) Int. Cl.
*A61M 5/178*  (2006.01)
*A61M 5/315*  (2006.01)
(Continued)

(52) U.S. Cl.
CPC .... *A61M 5/31568* (2013.01); *A61M 5/31553* (2013.01); *G01B 7/30* (2013.01);
(Continued)

(58) Field of Classification Search
CPC .......... A61M 5/31568; A61M 5/31533; A61M 5/31525; A61M 2205/3317;
(Continued)

(56) References Cited

U.S. PATENT DOCUMENTS 8,708,957 B2    4/2014  Jespersen et al.
10,155,090 B2 *  12/2018  Larsen .............. A61M 5/31525
(Continued)

FOREIGN PATENT DOCUMENTS

EP    2428238 A1    3/2012
EP    1646844 B2    8/2012
(Continued)

*Primary Examiner* — Nathan R Price
*Assistant Examiner* — Tania Ismail
(74) *Attorney, Agent, or Firm* — Levine Bagade Han LLP (57) ABSTRACT

The invention relates to a dose control system configured for an injectable drug delivery device. The device comprises a disk-shaped diametral single-dipole magnet (9) attachable to a rotatable dose wheel, a housing removably attachable to the proximal extremity of the drug delivery body and comprising at least a first and a second magnetic field measurement means (8). An integrated control unit (2) is connected to the magnetic field measurement means and is configured to process information received therefrom. The magnetic field measurement means are located in the housing in a displaced axial relationship relative to the longitudinal axis of the drug delivery body and the magnet. The magnet is configured to co-rotate with the dose setting wheel and the integrated control unit is configured to provide a normalized vector with regard to the displaced axial relationship of the magnetic field measurement means, said normalized vector being derived from the measured magnetic field generated by the rotation of the magnet and measured by the magnetic field measurement means. A dose setting is calculated from said normalized vector.

22 Claims, 3 Drawing Sheets

(51) Int. Cl.
*G01B 7/30* (2006.01)
*G01D 5/14* (2006.01)
*G05B 13/04* (2006.01)
*G16H 20/17* (2018.01)
*G16H 40/63* (2018.01)
*A61M 5/31* (2006.01)
*G01D 18/00* (2006.01)
*G01R 33/00* (2006.01)
*G01R 33/02* (2006.01)

(52) U.S. Cl.
CPC ........... G01D 5/145 (2013.01); G05B 13/041 (2013.01); G16H 20/17 (2018.01); G16H 40/63 (2018.01); *A61M 2005/3126* (2013.01); *A61M 5/31525* (2013.01); *A61M 2205/3317* (2013.01); *A61M 2205/3368* (2013.01); *A61M 2205/3553* (2013.01); *A61M 2205/3592* (2013.01); *A61M 2205/50* (2013.01); *A61M 2205/60* (2013.01); *A61M 2205/6054* (2013.01); *G01D 18/004* (2013.01); *G01D 18/008* (2013.01); *G01D 2205/22* (2021.05); *G01R 33/0017* (2013.01); *G01R 33/02* (2013.01)

(58) Field of Classification Search
CPC .. A61M 2205/3368; A61M 2205/6054; A61M 2205/60; A61M 2205/50; A61M 2205/3553; A61M 2205/3592; A61M 2005/3126; G01D 5/145; G01D 18/004; G01D 18/008; G01D 2205/22; G01R 33/02; G01R 33/0017; G01B 7/30
See application file for complete search history.

(56) References Cited

U.S. PATENT DOCUMENTS

2006/0175427 A1  8/2006  Jonientz et al.
2018/0200452 A1* 7/2018  Marcoz .............. G01R 33/0206

FOREIGN PATENT DOCUMENTS

| JP | 2012-519025 A | 8/2012 |
| JP | 2012-533058 A | 12/2012 |
| JP | 2014-531283 A | 11/2014 |
| JP | 2016-514554 A | 5/2016 |
| WO | WO 2002/064196 A1 | 8/2002 |
| WO | WO 2013/050535 A2 | 4/2013 |
| WO | WO 2014/161952 A1 | 10/2014 |
| WO | WO 2014/161954 A1 | 10/2014 |
| WO | WO 2015/158230 A1 | 10/2015 |
| WO | WO 2016/040949 A1 | 3/2016 |
| WO | WO 2017/013464 A1 | 1/2017 |

* cited by examiner

DOSE CONTROL SYSTEM FOR INJECTABLE-DRUG DELIVERY DEVICES AND ASSOCIATED METHODS OF USE

CROSS-REFERENCE TO RELATED APPLICATIONS

This application is a U.S. national application filed under 35 U.S.C. § 371 to International Application No. PCT/IB2017/000306 filed Jan. 25, 2017, the content of which is incorporated herein by reference in its entirety.

The present invention relates to the field of injectable-drug delivery devices, and in particular, to dose control systems provided for such injectable-drug delivery devices.

Delivery devices for injectable drugs have been known for many years. As demands have progressed and evolved for more patient responsibility in the management of their own individual treatments and medication plans, various drug delivery devices have been developed that allowed a user to self-inject their drug. This is particularly the case, for example, with insulin, intended to treat the consequences of diabetes. However, other drugs also fall into this category, required for example, to address potentially life-threatening situations, and enabling immediate emergency injection of a required drug, such as anaphylactic shock treatments, anti-coagulants, opioid receptor agonists and antagonists, and the like, to the extent that it has become a common occurrence for patients suffering from, or susceptible to, such ailments to carry these devices around with them.

One of the known problems with the existing self-injector systems was that of dosage control. In previous generations of injectable-drug delivery devices, such devices were equipped with mechanical means in order to attempt to prevent or limit excessive dose injections, or over use of the device, and the potentially serious consequences of such abuse, misuse, or simply user error. Additionally, it was felt desirable to be able to inform the user how much of the drug they had self-injected, so that there might be at least some visible cue as to the injected amounts, thereby facilitating management of the treatment regime.

The main problems associated with the mechanical solutions proposed was that they necessarily over-complexified the structure of the drug delivery devices, and quite often imposed a very strict or complicated modus operandi on the user, which often could be different to that to which the user was accustomed, thereby leading to yet further manipulation errors, lost drug doses, patient non-compliance, and numerous other difficulties.

To counter these difficulties, attempts were made to address the complex nature of purely mechanical solutions involving moving mechanical parts and mechanical interactions of small and fragile components, through the use of contactless sensors and an information processing system built into the device to indicate the frequency and dose amounts of injectable drug administered, wasted, purged or otherwise expelled from the drug delivery device. This led to multiple different technical solutions, however, each one was geared to the specifics of the particular manufacturer's corresponding range of injectable-drug delivery devices.

For example, in U.S. Pat. No. 8,708,957B2, a drug delivery device for self-injection of an injectable drug is disclosed comprising a sensor which is adapted to generate pulses during injection as the delivery movements progress. The number of pulses accumulated during dose delivery correspond to the size of the dose being delivered, whereas the frequency of the detected pulses is proportional to the dose speed during injection.

In other embodiments, the sensor circuitry can include position sensors adapted to monitor specific components of the drive mechanism which move during injection. The position sensors can be either linear sensors or rotary sensors, the particular choice of sensors being selected in accordance with the specific design of the dose setting and injection mechanism. For example, a linear position sensor can be provided that monitors the movements of the piston rod during injection. Alternatively, position sensors are provided which record the movements of a component which moves in synchronism with the piston rod during injection. For example, a component being rotatably mounted in the device and which rotates during injection may be monitored by a rotary position sensor whereby the dosing speed may be calculated from the rotary movement of the rotatably mounted component during injection.

EP1646844B2 discloses an injection device for administering an injectable drug, the device comprising a non-contact measuring unit for measuring a position between elements of a dosing device, and which can be moved relative to one another, the measuring unit comprising a magneto-resistive sensor, fixed to a first element, opposite a second magnetizable element, movable relative to the first element, and embodied as a rotational element for measuring rotational position; and a magnetic device formed from a permanent magnet on the first element, and a second magnetizable element with a predetermined surface profile such that when the first and second elements are moved relative to each other, a surface of the second element changes its distance from the permanent magnet of the first element, whereby a measurable change in resistance is generated in the magneto-resistive sensor due to the change in magnetic field. This is a fairly complex system with many additional moving parts built into the barrel, or body, of the injectable-drug delivery device, leading to a greater risk of potential failure of the various components, or potentially interfering interaction between the movements of the magnet and magnetizable elements, and the respective signals generated.

EP2428238A1 discloses an apparatus for measuring a dose in an injector, comprising a number sleeve that passes through an injector body and is connected to the injector body to be spirally movable, a pattern for dose measurement being formed on an outer periphery of the number sleeve; and the injector body comprising a sensor for sensing the pattern formed on the number sleeve when the number sleeve performs a spiral movement; and a controller for measuring a dose according to a spiral movement distance of the number sleeve through the sensor. In this device, a magnet is displaced spirally along the body of the drug delivery device, which is provided with corresponding sensors located at various points along and around the longitudinal axis of the body of the drug delivery device. Once again, this solution is extremely complex, and adds further complexity to an already complex drug delivery device.

WO 02/064196 A1 discloses an injection apparatus controlled by a closed switch unit comprising integrated sensors which monitor selected parameters of the apparatus. The closed switch unit is fixed within the injection apparatus. At least two pairs of integrated Hall elements are used as the sensors. The Hall elements co-operate with a magnetized ring which alternately exhibits north and south poles. The ring is arranged within a dosing means and is moved around the longitudinal axis of the injection apparatus in accordance with a rotational movement for setting a product dosage. In order to measure the volume of a dosage setting, it is necessary to determine the rotational movement of the magnetic ring relative to the closed switch unit.

US20060175427A1 discloses an injection apparatus comprising at least one passive, non-contact sensor which can generate signals for detecting the position of a setting element, the at least one passive, non-contact sensor comprising a magnetic switch or Reed contact. According to some embodiments of this invention, a passive component such as a magnetic switch or Reed contact may be used as the sensor, as opposed to using active components, such as optical recorders or Hall sensors. No power flows when the passive sensor is in its resting state due to the circuit being interrupted by the magnetic switch or Reed contact. The passive, non-contact sensor generates digital signals, i.e. ON and OFF, which switch on or activate a measuring circuit and switch it off again, in order to detect the position of a setting element by counting the switching-on and switching-off processes. The position of a setting element such as a rotational position of a dosing unit can be detected without energy, such as power, in order to ascertain whether a setting element has been altered or not.

WO2013050535A2 discloses a system comprising a sensor assembly adapted to measure a magnetic field, and a moveable element adapted to be moved relative to the sensor assembly between two positions by a combined axial displacement and rotational movement, the rotational movement having a pre-determined relationship to the axial displacement. A magnet is mounted to the moveable element and configured to generate a spatial magnetic field which relative to the sensor assembly varies corresponding to both the axial displacement and rotational movement of the magnet and thus the moveable element. A processor is configured to determine, based on previously measured and stored values of the magnetic field, an axial position of the moveable element. The example given in this system describes that the magnetic field producing means is located on a longitudinal drive screw that is located within the body of the injectable-drug delivery device, and the sensors are located along a longitudinal axis of said drug delivery device. The whole of the system is located within the main body of the drug delivery device. The technical teaching of this patent application focuses on the requirement to accurately determine the axial displacement of the movable element based on a lookup table of magnetic fields measured empirically in relation to any given angle of rotation, which thus necessitates that the magnetic field sensors be located close to the source of magnetic field.

WO2014161954A1 discloses a drug delivery system, wherein the housing of the drug delivery device further comprises, integrated inside said housing, a first rotational member adapted to rotate relative to the housing corresponding to a set and/or expelled dose and comprising a first force transmitting surface, a second rotational member adapted to rotate relative to the housing corresponding to a set and/or expelled dose and comprising a second force transmitting surface, wherein at least portions of the first and second force transmitting surfaces are adapted to engage each other during setting and/or expelling of a dose, wherein the first rotational member comprises a magnet producing a magnetic spatial field which varies corresponding to the rotational movement of the first rotational member, and wherein the first rotational member is fully formed from a polymeric material containing magnetic particles, the polymeric material having been magnetized to provide a magnet producing the magnetic spatial field.

All of the above solutions involve a fairly complex arrangement of various sensors and/or organisation of elements within the body of the drug delivery device, which moreover generally imply having to modify said drug delivery device fairly substantially, and additionally require calculation of axial displacement in order to determine an administered dose.

Accordingly, it is an object of the invention to provide a dose control system that can function with any of the currently available injectable-drug delivery devices, but which will also function with future designs of such injectable-drug delivery devices, to the extent that they rely on the general pen or cigar shape auto-injector design, and which does not require calculation or determination of axial displacement of the drive or lead screw or piston rod in order to accurately provide dosage information.

Additionally, it is another object of the present invention to provide such a dose control system which does not require substantial modification of the injectable-drug delivery device or the way in which it functions for the user, i.e. its modus operandi, when compared to a similar, off-the-shelf drug delivery device. It is yet another object of the present invention to provide a dose control system that is removably mounted on said injectable-drug delivery devices, such that the drug delivery devices can be exchanged, for example, in case of damage to the drug delivery device or malfunction in the drug delivery device, or simply because some drug delivery devices are configured to only deliver a small range of available doses of drug, and it is desirable to be able to switch to another drug delivery device that has a different range of available doses of drug.

A further object of the invention is to provide a dose control system for injectable drug delivery devices of the type described in the prior art, in which a magnetic field measurement means is located in a displaced axial relationship relative to the longitudinal axis of the drug delivery body.

These and other objects will become apparent from the various embodiments as indicated and detailed hereinafter.

BRIEF DESCRIPTION OF THE FIGURES

The invention will be further described in relation to the accompanying figures, provided for illustrative and non-limiting purposes of exemplary manifestations of the embodiments of the present invention, in which.

Accordingly, one embodiment of the present invention is a dose control system configured for an injectable drug delivery device, the drug delivery device comprising a substantially elongate drug delivery body, at least one injectable drug held by the body, the body having a distal and proximal extremity, and a rotatable dose setting wheel located at a proximal extremity of said drug delivery body, rotatable about a longitudinal axis of said drug delivery body, wherein the dose control system comprises:

- a substantially disk-shaped diametral single-dipole magnet removably attachable, or permanently fixed, to the rotatable dose wheel at the proximal extremity of said drug delivery body;
- a housing removably attachable to the proximal extremity of the drug delivery body, the removably attachable housing comprising:
    - at least a first and a second magnetic field measurement means configured to measure the magnetic field produced by the substantially disk-shaped diametral single-dipole magnet;
    - an integrated control unit connected to the at least first and second magnetic field measurement means configured to process information received from the at least first and second magnetic field measurement means;

wherein:
- the at least first and second magnetic field measurement means are located in the removably attachable housing in a displaced axial relationship relative to the longitudinal axis of the drug delivery body and the substantially disk-shaped diametral single-dipole magnet;
- the substantially disk-shaped diametral single-dipole magnet is configured to co-rotate with said dose setting wheel around the longitudinal axis of the drug delivery body; and
- the integrated control unit being further configured to:
    - provide a normalized vector with regard to the displaced axial relationship of the magnetic field measurement means, said normalized vector being derived from the measured magnetic field generated by the rotation of the substantially disk-shaped diametral single-dipole magnet and measured by the magnetic field measurement means, and
    - calculate a dose setting from said normalized vector.

In a further embodiment of the invention, the integrated control unit is configured to calculate corrected offset values for said at least first and second magnetic field measurement means.

According to still yet another embodiment of the present invention, the at least first and second magnetic field measurement means are located in the removably attachable housing adjacent to the proximal extremity of the drug delivery device body.

In another embodiment of the invention, the at least first and second magnetic field measurement means are located distally from the proximal extremity within said housing.

According to yet another embodiment, the at least first and second magnetic field measurement means are located on a support structure located within the housing.

In yet another embodiment, the first magnetic field measurement means and the second magnetic field measurement means are in axial alignment one with the other.

According to yet another embodiment, the at least first and second magnetic field measurement means are magnetometers, wherein the first magnetometer and the second magnetometer are configured to simultaneously and independently measure the magnetic field produced as the substantially disk-shaped diametral single-dipole magnet is rotated about the longitudinal axis of the drug delivery device body.

According to still another embodiment, the at least first and second magnetic field measurement means are further configured to measure the magnetic field produced as the substantially disk-shaped diametral single-dipole magnet translates along the longitudinal axis of the drug delivery device body.

In a system such as the one according to the present invention, the first and second magnetometers are located on a support structure, for example, a printed circuit board, on which the other elements of the integrated processing unit are also mounted. Spatially, and relative to three orthogonal axes x, y, and z, where the y axis corresponds to the longitudinal axis of the drug delivery device body, this configuration can be expressed mathematically for the first magnetometer m1 as follows:

$$\begin{bmatrix} x \\ y \\ z \end{bmatrix} = \begin{bmatrix} -m1_x \\ m1_y \\ -m1_z \end{bmatrix}$$

A similar representation exists for the second magnetometer m2.

$$\begin{bmatrix} x \\ y \\ z \end{bmatrix} = \begin{bmatrix} m2_x \\ m2_y \\ m2_z \end{bmatrix}$$

and the relationship between m1 and m2 is expressed as:

$$\begin{bmatrix} -m1_x \\ m1_y \\ -m1_z \end{bmatrix} = \begin{bmatrix} m2_x \\ m2_y \\ m2_z \end{bmatrix}$$

In a theoretically ideal system, a magnetic field measurement means, such as a magnetometer would be positioned in axial alignment and as close as possible to the magnetic field producing means. When applied to a drug delivery device body, this would imply that the magnetometer would have to be located along the longitudinal axis of the device body. In such a theoretical, ideal system, there would also be no magnetic field disturbances. All of the magnetic fields generated by the magnet within the system would be coplanar with a plane that is perpendicular to the longitudinal axis of the drug delivery device body. All of the magnetic fields generated by the magnet within the system would have a normal that is directly linked to the distance between the magnet and the magnetometers. In other words, the magnetic fields produced and measured would be directly correlatable to translation of the magnet along the longitudinal axis of the drug delivery device body, irrespectively and independently of any angle of rotation of the magnet. In such an ideal system, the angle of rotation of the magnet would be correctly calculated, except for minor magnetic field disturbances, by using two of the three polar coordinates of the measured magnetic field.

Where:

$$\begin{bmatrix} x_{field} \\ y_{field} \\ z_{field} \end{bmatrix}$$

are the coordinates of any given measured magnetic field, then the angle of rotation can be calculated as follows:

$$\text{angle}_{rotation} = a\tan 2(z_{field}, x_{field})$$

In the real world, however, systems do not behave ideally, and the ideal, hypothetical configuration identified above can not be obtained. In a system according to the present invention, the magnetic field measurement means, whilst in axial alignment to the longitudinal axis of the drug delivery device body, are not co-aligned with the rotational axis of the substantially disk-shaped magnet, but are nonetheless substantially parallel to the longitudinal axis of the drug delivery device body. Such a configuration produces several undesired effects, among which:
- the normal projections for each magnetic field measured vary as a function of both
  - (a) the distance of the magnet along the longitudinal axis of the drug delivery device body, and
  - (b) the angle of rotation of the magnet which, because of the displaced, non-axial alignment of the magnetic field measurement means, creates an oscillation in the distance, and thus of the normal projection, relative to the maximum magnetic field potential of the magnet;
- the difference in angle of the measured magnetic fields relative to the angle of a normal projection varies as a function of both the distance and the angle of rotation, in other words, they are no longer coplanar.

Additionally, other errors also present in real systems need to be accounted for, including:
- offset and calibration errors due to each magnetometer;
- sensitivity errors particular to each magnetometer, and for each measurement made;
- errors caused by external magnetic field disturbances, although this is mainly the earth's own magnetic field;
- errors induced by mechanical tolerance in the components making up the system.

In the light of the above, a real-life system configuration no longer enables correct calculation of the angle of rotation in the naïeve manner indicated for a hypothetically ideal system. Any approximations made with regard to the projection along the XZ plane will tend to introduce major errors, due mainly to change in the difference of angles and a normal projection that varies with the angle of rotation of the magnet. Additionally, as the magnetic field normal also varies with any translational distance moved by the magnet in combination with rotation of the magnet, any effective interpretation of a true angular rotation position of the dose selecting wheel becomes extremely problematic.

The system according to the present invention resolves these difficulties, and additionally provides a means for calculating accurate angle of rotation, and hence dose wheel setting, which is not affected by the non-axial alignment of the magnetic field measurement means with the substantially disk-shaped diametral dipole magnet. Furthermore, the system according to the present invention, through the use of corrected and accurately calculated angles of rotation, also optionally and advantageously enables accurate calculation of any translational distance of the magnet along the longitudinal axis of the drug delivery device body, should such a calculation be desirable.

Whilst errors caused by mechanical interactions of the components making up the device, and errors caused by the relative sensitivities of the magnetic field measurement means have been mentioned as possible sources of errors in the calculations of correct rotational angle, these sources are considered negligible in the system according to the present invention and have thus been ignored.

Accordingly, in another embodiment of the dose control system according to the invention, the integrated control unit is further configured to calculate offset values for said magnetic field measurement means via the formula:

$$\begin{bmatrix} x_{offset} \\ y_{offset} \\ z_{offset} \end{bmatrix} = \begin{bmatrix} \frac{(\max(f_x \cdot x_i) + \min(f_x \cdot x_i))}{2} \\ \frac{(\max(f_y \cdot y_i) + \min(f_y \cdot y_i))}{2} \\ \frac{(\max(f_z \cdot z_i) + \min(f_z \cdot z_i))}{2} \end{bmatrix}$$

where x, y and z are the three orthogonal axes of magnetic field, and:
$x_i$, $y_i$, and $z_i$ are a series of points generated by corresponding vectors of the measured magnetic fields resembling a cloud of points in three dimensions, said cloud of points being sphericized by the factors:

$$\begin{bmatrix} x_i \\ y_i \\ z_i \end{bmatrix} = \begin{bmatrix} f_x \cdot x_i \\ f_y \cdot y_i \\ f_z \cdot z_i \end{bmatrix}$$

According to another embodiment, the magnetic offset values are corrected via the formula:

$$\begin{bmatrix} x_{corrected} \\ y_{corrected} \\ z_{corrected} \end{bmatrix} = \begin{bmatrix} f_x \cdot x_i - x_{offset} \\ f_y \cdot y_i - y_{offset} \\ f_z \cdot z_i - z_{offset} \end{bmatrix}$$

If the magnetometers are optionally and advantageously pre-calibrated, the sphericizing factors $f_x$, $f_y$ and $f_z$ are equal to 1 and thus no longer necessary in the above offset value correction formula.

In yet another embodiment, when the first and second magnetometers are further configured to cancel out any external magnetic fields that can negatively influence the dose control system. When a negative external magnetic influence occurs, both the first and second magnetometers, identifiable for the present explanation, as m1 and m2, are subjected to the same external magnetic fields. The situation can be represented as follows:
- CMm1: the magnetic field measured by magnetometer m1
- CMm2: the magnetic field measured by magnetometer m2
- CAm1: the actual magnetic field generated by the magnet, as measured by magnetometer m1
- CAm2: the actual magnetic field generated by the magnet, as measured by magnetometer m2
- CE: the external magnetic field and the relationship between these components defined as follows:

$$CM_{m1} = CA_{m1} + CE$$

$$CM_{m2} = CA_{m2} + CE$$

The external magnetic field can be cancelled out by letting CR be a pseudo-resultant magnetic field defined as follows:

$$CR = CM_{m1} - CM_{m2} = (CA_{m1} + CE) - (CA_{m2} + CE) = CA_{m1} - CA_{m2}$$

$CA_{m1}$ and $CA_{m2}$ evolve similarly one relative to the other, in a quasi-parallel manner, and functionally dependent on the distance between magnetometer $m_1$ and magnetometer $m_2$. As a result, CR can be described as a pseudo-vector representing a resultant pseudo-magnetic field calculated from the measured magnetic fields $CA_{m1}$ and $CA_{m2}$, and the value of CR is comprised between the values of $CA_{m1}$ and $CA_{m2}$, whereby said pseudo-vector evolves in a similar manner to said measured magnetic fields, i.e. quasi-parallel to $CA_{m1}$ and $CA_{m2}$. CR is thus representative of the angle of rotation of the magnet, and thereby the dose selector wheel, independently of any system-external magnetic field disturbances. As $CA_{m1}$ and $CA_{m2}$ display a linked evolving normal, if the normal of $CA_{m1}$ increases, that of $CA_{m2}$ does so too, and the reciprocal is true. The following relationship is therefore also always true:

$$|CAm1| > |CAm2|$$

Consequently, in yet another embodiment of the present invention, the integrated processing unit is configured to correct magnetic field values measured by the magnetic field measurement means as a function of the non-axial alignment of the magnetic field measurement means relative to the substantially disk-shaped diametral single-dipole magnet.

In a further embodiment, the integrated processing unit is configured to correct magnetic field values measured by the magnetic field measurement means and resulting from a lack of axial alignment of the magnetic field measurement means with the substantially disk-shaped diametral single-dipole magnet by applying a rotation to a pseudo-vector representing a resultant pseudo-magnetic field calculated from the measured magnetic fields of said first and second magnetic field measurement means, around one of three orthogonal axes x, y or z, to bring said pseudo-vector representing said resultant pseudo-magnetic field into an iso-normal projection.

In yet another embodiment, the integrated processing unit is configured to correct magnetic field values measured by the magnetic field measurement means and resulting from a lack of axial alignment of said magnetic field measurement means with the substantially disk-shaped diametral single-dipole magnet, through application of the following calculation, in which, in a system with three orthogonal axes, X, Y and Z, d equals the distance between the proximal extremity of the drug delivery device body and the substantially disk-shaped magnet along the Y-axis. For each distance d, a plane exists that passes through the X axis, such that the projection of magnetic fields which are coplanar with said plane, along the plane XZ, are all equi-normal, irrespectively and independently of the angle of rotation of the magnet. This plane is known as the iso-normal projection. This calculation can be expressed as follows:

$R_x$ is an angle, indicated in degrees, enabling transformation of a magnetic field pseudo-vector by rotation around an orthogonal axis, preferably the X axis, to position said magnetic field pseudo-vector, such that said pseudo-vector becomes substantially co-planar with its iso-normal projection.

$\ominus_x$ is the actual measured angle of rotation, in degrees, about the X axis, whereby:

$$\theta_x = \operatorname{atan}\left(\frac{CR_z}{CR_y}\right), \text{ and}$$

$$R_x = \frac{\log\frac{1}{\theta_x + c_2} - c_1}{c_3} x c_4 + c_5$$

In the above formula, $c_1$ to $c_5$ are constants which are calculated for each system and which take into account, and among others:

the relative spatial locations of said first magnetometer ($m_1$) and said second magnetometer ($m_2$);
the physical characteristics of said first and second magnetometers;
the magnetic field producing capacity of the substantially disk-shaped diametral single-dipole magnet;
the size of the substantially disk-shaped diametral single-dipole magnet;
distance d
and other optional parameters as deemed appropriate.

Factors or constants $c_1$ to $c_5$ can be determined as follows:
a data set is generated for a representative subset of values of magnetic field. The data is generated for a representative variety of distances d. A simulation software program or library suitable for use in such simulated data generation, is that made available by Infineon, and known as the "3D Magnetic Sensor Design Tool", accessible via the following web page URL: http://design.infineon.com/3dsim/#/
$R_x$ is approximated as a function of $\ominus_x$ for each simulation, whereby the difference between the normals of each projected magnetic field vector is minimized relative to the iso-normal projection;
$R_x$ is modelled for values of $\ominus_x$ for each distance d leading to a set of values $d_i$, $\ominus_{xi}$ and $R_{xi}$, the values given below being merely illustrative for purposes of an example in relation to one particular system:

| d | $\theta_x$ | $R_x$ |
|---|---|---|
| 0 | −12.21 | 35.15 |
| 2.8398 | −5.3 | 37.8 |
| 12.3058 | 12.12 | 45.07 |
| 17.0388 | 18.59 | 47.93 |
| 21.7718 | 24.07 | 50.55 |
| 31.2378 | 32.56 | 54.72 | where $R_x$ can be modelled as follows:

$$R_x = \frac{\log\frac{1}{\theta_x + V_{adjust}} - p_1}{p_2 - p_1} * (p_4 - p_3) + p_3$$

where:

$$p_1 = \min\left(\log\frac{1}{\theta_{xi} + V_{adjust}}\right)$$

$$p_2 = \max\left(\log\frac{1}{\theta_{xi} + V_{adjust}}\right)$$

$$p_3 = \max(R_{xi} - \theta_{xi})$$

$$p_4 = \min(R_{xi} - \theta_{xi})$$

$V_{adjust}$ is an adjustment variable for minimizing error between approximated values of $R_x$ obtained via simulation and the values of $R_x$ calculated by the system.

From the above, the following attributions can be made for the factors $c_1$ to $c_5$:

$c_1 = p_1$
$c_2 = V_{adjust}$
$c_3 = p_2 - p_1$
$c_4 = p_4 - p_3$
$c_5 = p_3$

Suitable example values of $c_1$ to $c_5$ for use in the system according to the invention can be:

$c_1 = -2.31864756900365$
$c_2 = 175.72$
$c_3 = 0.105103250465988$
$c_4 = 25.2$
$c_5 = 22.16$

In another embodiment, the integrated processing unit is configured to apply a low and high cut-off value to limit $R_x$ values obtained during processing in order to help avoid amplification of reading errors into the calculations. This can be achieved for example, via the use of a function such as $\min(\Theta_x)$ and $\max(\Theta_x)$ respectively, for the low and high cut-offs at the operating limits of the functioning system.

In a further embodiment of the invention, the dose control system further comprises communication means configured to enable communication of information from the integrated control unit with a remote and/or local data processing system.

In yet another embodiment of the invention, the remote and/or local data processing system comprises a smartphone application.

In still another embodiment of the invention, the dose control system further comprises a unique identifier that is communicated to the remote and/or local data processing system.

In another embodiment of the invention, the dose control system further comprises temperature detection means.

In another embodiment of the invention, the dose control system further comprises time determination means.

In a further embodiment of the invention, the dose control system further comprises autonomous power supply means.

In still yet another embodiment of the present invention, said dose control system is configured to permit an unhindered or unchanged modus operandi of said drug delivery system when compared to an off the shelf injectable-drug delivery device.

In yet another embodiment of the invention, there is provided a method for calculating a dose setting in a dose control system as substantially described and exemplified herein, said method comprising the steps of:
  measuring a magnetic field (CM) produced by a rotatable substantially disk-shaped diametral single-dipole magnet with at least a first ($m_1$) and a second ($m_2$) magnetometer disposed in displaced axial alignment to an axis of rotation of said magnet;
  calculating a resulting magnetic field pseudo-vector (CR);
  optionally correcting said measured magnetic field CMm1 and CMm2;
  calculating the angle of rotation to an iso-normal plane of projection for said magnetic field pseudo-vector;
  transforming said magnetic field pseudo-vector with said angle of rotation to create, by rotation and projection, an iso-normal corrected magnetic field pseudo-vector (CR2);
  calculating from said corrected iso-normal magnetic field pseudo-vector an angle of rotation of said magnet about said axis of rotation.

In yet another embodiment of the method above, the method further comprises calculating a reference position of said magnet on a normal corresponding to a translated position of said magnet along said axis of rotation.

As mentioned in the various embodiments of the invention, the dose control system comprises a substantially disk-shaped diametral single-dipole magnet which is removably attachable to, or permanently fixed to, the dose wheel selector of the drug delivery device. The magnetic field produced by such a magnet extends spatially around said magnet in a known manner, and this magnetic field can be measured by an appropriately provided magnetic field measurement means. As will be seen with regard to the further description of the invention, this field is used to calculate an angular rotational position, and optionally additionally, but advantageously, a position along the normal, which in the present case is along the longitudinal axis of the drug delivery device body. Once that angular rotational position, or optionally and advantageously the normal, is known with accuracy, as provided by the system of the present invention, said system can, due to the fact that the substantially disk-shaped diametral single-dipole magnet is positioned at the proximal extremity of, or attached to said dose selector wheel in a rotatably-operable manner, calculate a corresponding dose setting of the dose selector wheel and advantageously communicate said value to the user, a healthcare professional or local or remote data processing system such as a local or remote computer, server, distributed data storage facility, or other form of digital data storage and communication facility.

Various means for producing a magnetic field are known, for example, classical magnets, electromagnets, mixed material magnets. Such magnets are typically made from magnetizable materials, having magnetic or paramagnetic properties, whether naturally or when an electric or other energizing flow traverses or affects said material to produce or induce a magnetic field in said material. Suitable materials can be appropriately selected from:

ferrite magnets, especially sintered ferrite magnets, for example, comprising a crystalline compound of iron, oxygen and strontium;
  composite materials consisting of a thermoplastic matrix and isotropic neodymium-iron-boron powder;
  composite materials made up of a thermoplastic matrix and strontium-based hard ferrite powder, whereby the resulting magnets can contain isotropic, i.e. non-oriented, or anisotropic, i.e. oriented ferrite particles;
  composite materials made of a thermo-hardening matrix and isotropic neodymium-iron-boron powder;
  magnetic elastomers produced with, for example, heavily charged strontium ferrite powders mixed with synthetic rubber or PVC, and subsequently either extruded into the desired shape or calendering into fine sheets;
  flexible calendered composites, generally having the appearance of a brown sheet, and more or less flexible depending on its thickness and its composition. These composites are never elastic like rubber, and tend to have a Shore Hardness in the range of 60 to 65 Shore D ANSI. Such composites are generally formed from a synthetic elastomer charged with strontium ferrite grains. The resulting magnets can be anisotropic or isotropic, the sheet varieties generally having a magnetic particle alignment due to calendaring;
  laminated composites, generally comprising a flexible composite as above, colaminated with a soft iron-pole plate;
  neodymium-iron-boron magnets;
  steels made of aluminium-nickel-cobalt alloy and magnetized;
  alloys of samarium and cobalt.

Of the above list of magnetic field producing means suitable for use in the substantially disk-shaped, diametral single-dipole magnet implemented in the present invention, neodymium-iron-boron permanent magnets are preferred. Such magnets are known for their ability to be dimensioned at relatively small sizes whilst maintaining relatively high magnetic field strength. Although the absolute magnetic field strength of the substantially disk-shaped, diametral single-dipole magnet implemented in the present invention is not essential to correct functioning of the system according to the invention, it is preferred that both the field strength of the magnet and the positioning of the magnetic field measurement means are configured in such a way that a difference of at least 100 microTesla ($\mu$T) is present between the values measured at the first magnetic field measurement means and the second magnetic field measurement means.

By "substantially disk-shaped", it is to be understood that the magnet defines a general disk shape, which could be circular, elliptoid, or even any suitable polygonal shape, and has only a single dipole, in other words, a single pair of diametrically opposing north and south magnetic poles. As indicated above, although the magnet used in the present invention is substantially disk-shaped, such substantial disk-shape can also include magnets which have an orifice substantially in the center of the disk to form a ring or annular shaped magnet.

The magnet of the present invention is configured to effect axial rotation around, and optionally translate along, the longitudinal axis of the drug delivery system. The rotating displacement coincides with that of a dose selector wheel, meaning that turning the magnet around the longitudinal axis causes said dose selector wheel to rotate in the same direction. Generally, the dose selector wheel is attached to a drive shaft or lead screw, which traverses an interior bore of the drug delivery device body. As is generally applicable to drug delivery devices equipped with such dose selector wheels, the magnet can translate longitudinally with the dose selector wheel both away, i.e. proximally, from the proximal extremity of the body of the drug delivery device, when increasing the dose to be injected and in the opposite direction, translating longitudinally along the longitudinal axis of the device distally, back towards the proximal extremity of the device as the dose is reduced. In such a configuration, the system can also calculate distance of travel along the longitudinal axis in an optional and advantageous embodiment. In another embodiment, the dose selector wheel is not configured to effect longitudinal translation, meaning that the dose selector wheel is simply configured to rotate about the longitudinal axis, and that this rotational movement defines the doses selected, whether clockwise or counter-clockwise. The dose control system according to the present invention is naturally configured to function appropriately in any of these configurations.

In addition, the magnetic field producing means is dimensioned to provide sufficient magnetic field to be detected by the magnetic field measurement means, and thereby hinder the user or usage of the drug delivery device in normal operation when compared to a drug delivery device that has no such dose control system according to the invention.

In the dose control system according to the present invention, at least a first and a second magnetic field measurement means are present and configured to measure the magnetic field produced by the substantially disk-shaped magnet. The at least first and second magnetic field measurement means are used to measure the magnetic field produced by rotational, and optionally translational, movement of the substantially disk-shaped magnet, to calculate an angular rotational position of the magnetic field producing means in order to accurately determine which dose has been selected for administration via the injectable-drug delivery device, Optionally, and advantageously, such a system can also be used to calculate a translational position of a reference point of interest along the longitudinal axis of the drug delivery device body, which reference point can be used to correlate to a dose administered, a zero point, priming point, or initialization point for the system, a start point for injection, and/or an end point for injection.

Means for measuring magnetic fields to determine a rotational angular position are known generally in the art. For example, magneto-resistors are a well known means, some of which are used in the prior art systems. Such magneto-resistors are often designated by their abbreviations, e.g. AMR, GMR, TMR sensors, which designate the physical mechanisms by which these sensor components function. Giant magnetoresistance (GMR) is a quantum mechanical magnetoresistance effect observed in thin-film structures composed of alternating ferromagnetic and non-magnetic conductive layers. Anisotropic magnetoresistance, or AMR, is said to exist in materials in which a dependence of electrical resistance on the angle between the direction of electric current and direction of magnetization is observed. Tunnel magnetoresistance (TMR) is a magnetoresistive effect that occurs in a magnetic tunnel junction (MTJ), which is a component consisting of two ferromagnets separated by a thin insulator. Resistors that use these various properties are known per se.

In light of the above, the dose control system of the present invention preferably uses magnetometers, and preferably at least a first and second magnetometers. These magnetometers differ from the GMR, AMR or TMR sensors in that they directly measure magnetic field strength. Magnetometers measure magnetic fields in two main ways: vector magnetometers measure the vector components of a magnetic field, and total field magnetometers or scalar magnetometers measure the magnitude of the vector magnetic field. Another type of magnetometer is the absolute magnetometer, which measures the absolute magnitude or vector magnetic field, using an internal calibration or known physical constants of the magnetic sensor. Relative magnetometers measure magnitude or vector magnetic field relative to a fixed but uncalibrated baseline, and are also called variometers, used to measure variations in magnetic field.

A suitable and preferred magnetometer for use in the dose control system according to the present invention is an ultra low-power high performance three axis Hall-effect magnetometer. Whilst it is possible for the magnetometer to be configured to measure magnetic field over three mutually perpendicular or orthogonal axes, it is nonetheless preferred that the magnetic field measurement means be configured to measure magnetic fields over just two of the three orthogonal axes, for example the X and Z axes, whereby the Y axis, in an example system of the present invention, is co-axial with the longitudinal axis of the drug delivery device body and thereby corresponds to the normal along which distance measurements relating to translational movement of the dose selector wheel along said longitudinal axis can be calculated as indicated above in respect to a reference point position on said axis.

The dose control system also advantageously comprises an integrated control unit connected to the magnetic field measurement means for processing information received from the magnetic field measurement means. This integrated control unit can be mounted on a printed circuit board, for example, of suitable dimensions, e.g. approximately 45 mm long by 15 mm wide, and 1.5 mm deep. The integrated control unit handles all electrical communication and signalling between the different electronic components of the dose control system. It is also responsible for execution of the dose management system and calculations enabling the precise positional location of the magnet to be calculated and determined, as well as handling signals from the autonomous power means and the communication means, with a local or remote data processing system, e.g. on a smartphone. It can be programmed remotely, upon first use, or receive information and updates, in a similar way to other electronic devices today containing integrated control units. Such integrated control units are known per se, and often integrate a central processing unit, a real time clock, one or more memory storage systems, and optionally communications systems or subsystems, along with other desired components.

The dose control system of the present invention marks a clear break with the past solutions, by providing a dose control system, that is not only removably mounted on the body of the drug delivery device, but is also capable of accurately providing calculation of angular position, or optionally and advantageously the normal, through measurement of magnetic field, and thereby calculating the corresponding selected dose, without having to place all of the components within the body of the drug delivery device itself and co-axially with or in close proximity to, the longitudinal axis of the drug delivery device body. In fact, the dose control system of the present invention has enabled the applicants to provide a removably mountable system, that can be used with a variety of different drug delivery devices currently on the market, in particular, but not exclusively, the insulin auto-injector pens that are currently distributed for patient self-medication.

DETAILED DESCRIPTION

Figure 1:
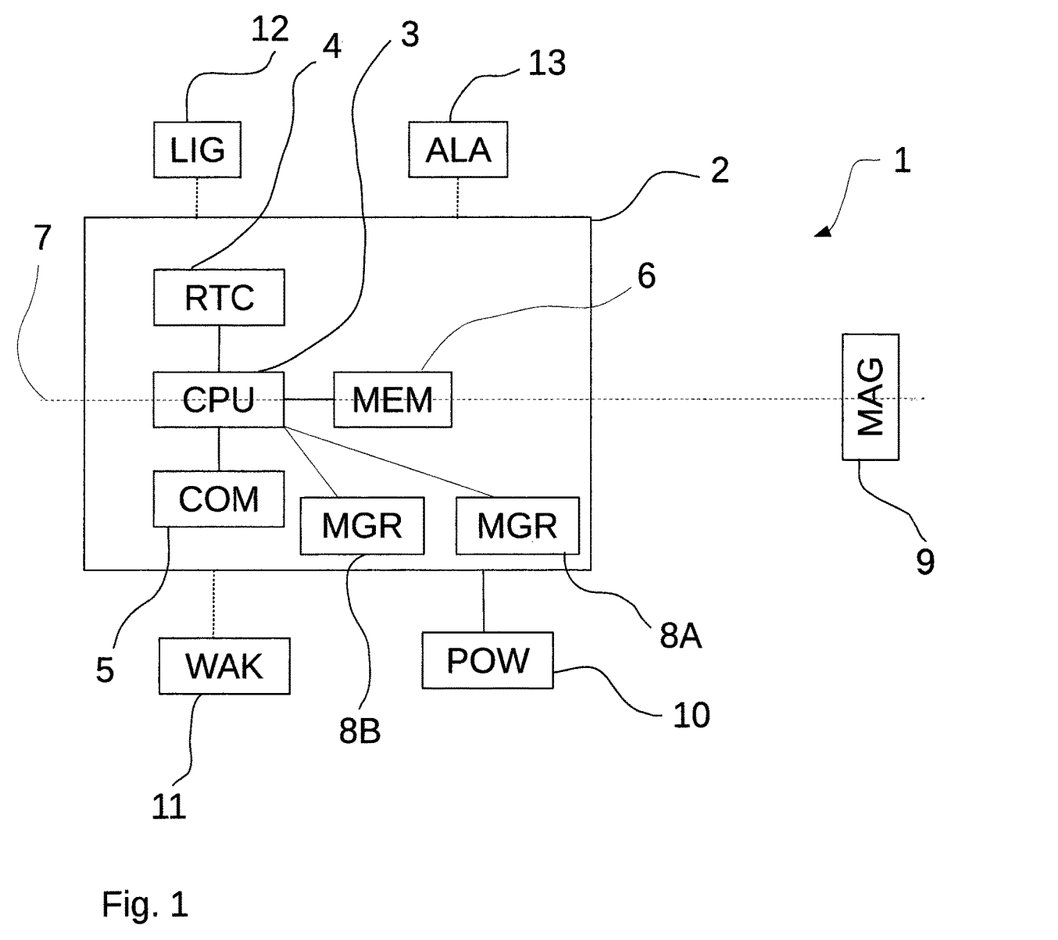
FIG. 1 is a schematic view of an example of a dose control system according to the present invention.

Turning now to FIG. 1, a schematic diagram of the components of a dose control system (1) according to the present invention is displayed. Such a dose control system comprises for example, an integrated control unit (2), for example, mounted on a printed circuit board, or equivalent on which various components are mounted and in connection with each other. The integrated control unit (2) could also be comprised of circuits engraved or etched in silicon or the like, as is known per se. In fact, virtually the whole dose control system could be engraved into a single, or multiple, interconnected blocks of silicon or other similar semi-conductor material as generally known in the art if so desired. The integrated control unit (2) comprises a central processing unit (CPU, 3), which is responsible for processing and managing signals and communication between the various components of the system, and also for calculations, and execution of program code stored within the system, or operable remotely on said system. The integrated control unit (2) can additionally comprise a real time clock (RTC, 4), for keeping and measuring time within the dose control system. The real time clock (RTC, 4) can also be integrated directly into the central processing unit (CPU, 3), for example, using frequency measurements whilst the central processing unit (CPU, 3) is powered with energy, in order to calculate time and time differences for various events within the system. The dose control system is also preferably equipped with a communications subsystem (COM, 5), for example a low power consuming bluetooth radio device, the communications subsystem allowing for the dose control system to communicate with a local or remote data processing system (not shown), e.g. a PC, a server, distributed data storage, or other digital data storage facility, or even a smartphone and corresponding smartphone application, used to provide information and feedback to the user on usage of the dose control system. Additionally, the system also preferably has some form of memory storage (MEM, 6), for storing information within the system, whether transiently or permanently, such information coming from a variety of sources, including the values or signals measured or determined from other endpoints of the system, values calculated or stored by the central processing unit (CPU, 3), values or data received from the remote or local data processing system, such as the smartphone, factory settings for calibration of the system, a unique identifier means or data identifying the device uniquely, and the like. Such memory storage systems (MEM, 6) are known per se to the skilled person.

The integrated control unit (2), and by extension, the central processing unit (CPU, 3), is also in communication with at least a first magnetometer (MGR, 8A) and a second magnetometer (8B). As illustrated on the figure, the magnetometers (MGR, 8A, 8B) are also connected to the central processing unit (CPU, 3). These components are responsible for measuring the magnetic field produced by the substantially disk-shaped diametral single-dipole magnet (MAG, 9), which is in a movable spaced relationship with the magnetometers (MGR, 8A, 8B), and shows an axis of rotation 7 which is also co-axial with the axis of a drug delivery device body (not shown). The magnetometers are capable of measuring magnetic field along multiple axes, for example one, two, three or more axes, although measurements are preferably made along three axes, which are designated as the X, Y and Z axes. In the schema of FIG. 1, the Y axis is co-axial with the axis of rotation of the magnet (MAG, 9). Usually, these axes are perpendicular to one another, so as to provide a three-dimensional magnetic field measurement zone. The at least two magnetometers (MGR, 8A, 8B) are located so as to be able to measure magnetic field produced by the magnet (MAG, 9) as the latter is displaced, either rotationally about, or translationally along and/or both rotationally and translationally about and along, the axis of rotation 7, and thus also the longitudinal axis of the drug delivery device body on which the system would be mounted. As can be seen from FIG. 1, the system includes two magnetometers (MGR 8A, 8B) which are displaced from the axis of rotation 7, but parallel to this axis, and hence parallel to the longitudinal axis of the drug delivery device body.

The substantially disk-shaped diametral single-dipole magnet (MAG, 9) produces a magnetic field which is measured along three perpendicularly positioned axes X, Y, Z. As mentioned above, the magnetometers (MGR, 8A, 8B) measure the magnetic field produced by the magnet (MAG, 9), not only when the latter rotates, but also optionally and advantageously when it undergoes a translational movement, for example, proximally, and away from, or distally and towards, a proximal extremity of the drug delivery device. This detection of magnetic field changes occurs without any form of electrical or electronic or physical contact between the magnetometers (MGR, 8A, 8B) and the magnet (MAG, 9), leading to the designation of the dose control system as a contactless system.

The substantially disk-shaped magnet is removably attachable, or permanently fixed, to a dose setting wheel located at the proximal extremity of the drug delivery device body and can be made of any suitable magnetic or magnetizable material, details of which are given elsewhere in the present specification, but preferably is a neodymium-ironboron permanent magnet. The magnet (MAG, 9) can thus be mounted via the dose selector wheel onto a dose selector shaft of the drug delivery device, which is in longitudinal axial alignment with the longitudinal axis of the drug delivery device body. The magnet is removably mounted, or permanently fixed, to the dose selector wheel in such a way that it can impart rotational movement to said wheel when turned by a user. Rotation can occur in both clockwise and counter-clockwise directions. The magnet has two opposing poles, each substantially constituting a half, or hemispherical part of the substantially disk-shaped magnet. As the magnet rotates, the opposing poles also rotate around the longitudinal axis of the drug delivery device body. The system can optionally be zero-pointed, i.e. a zero-point reference can be taken by measuring the magnetic field produced when the magnet is first attached to the dose selector wheel. The dose control system in general is calibrated beforehand at the factory or manufacturing unit, including basic calibration of the magnetometers. If a zero point reference is taken, it can be stored in memory (MEM, 6), via the central processing unit (CPU, 3). Where translational movement of the dose selector wheel is permitted, optionally, and for certain types of injector pen drug delivery devices, on first initialization this optional base reference or zero-point magnetic field can be set to correspond to a translational position of the magnet (MAG, 9) in which it is closest to the proximal extremity of the drug delivery device, and beyond which further rotation of the dose selector wheel in a distal direction is impossible. When the user rotates the magnet (MAG, 9), in an allowed direction of rotation, the dose selector wheel rotates accordingly, the magnet and dose selector wheel move longitudinally in a proximal direction away from the proximal extremity of the body of the drug delivery device, but along the longitudinal axis of the device in general. When the user has stopped rotating the magnet (MAG, 9) and corresponding dose selector wheel, the magnetometers (MGR, 8A, 8B) can then, for example, measure the magnetic field produced by the magnet at that distance. The measured magnetic fields at each magnetometer can be resolved into mathematical components comprising vectors and moduli by the integrated processing unit (CPU, 3), and therefrom an angular position of rotation calculated, allowing for extremely precise determination of the angular position and distance of the magnet with respect to the magnetometer(s) (MGR, 8A, 8B). From that angle of rotation and distance, an accurate, selected dose can, for example, be calculated. Dose values calculated by the dose control system are preferably stored within the system, or alternatively stored within a remote data processing or storage unit, such as a PC, server, cloud service, distributed digital storage, or smartphone, wherein the maximum and minimum distances of allowed travel and rotation of the magnet (MAG, 9) along the longitudinal axis correspond to the maximum and minimum dosages allowed by the drug delivery device. In this way, the dose control system is able to present to the user an exact representation of the dose selected by the user at any given rotational, and optionally translational, movement point of the magnet (MAG, 9), without interfering or changing the usual modus operandi of the drug delivery device. Preferably, the dose control system has a resolution equal to an angular rotation of the magnet of greater than or equal to 0.01° about the longitudinal axis, but as mentioned above, the resolution and sensitivity of the various components can be configured to correspond to any drug delivery device that functions in a similar manner.

Also represented in FIG. 1 are a power supply (POW, 10), which is generally a portable, autonomous power supply, for example, one or more batteries, or rechargeable power elements, capable of supplying sufficient electrical power to the entire system, even when for example, the device is not being directly manipulated. The integrated control unit (2) can additionally comprise a power management unit, that regulates power supply voltage to the system, including its various components, in order to maximise the longevity of said autonomous power supply. The power supply can also communicate with a user-activated wake-up button (WAK, 11) which allows the dose control system to be woken up by the user from a hibernating or sleeping state.

The dose control system can also further comprise a light emitting signal (LIG, 12), for example, a LED, which indicates a status of the device according to detected events or conditions and managed by the central processing unit (CPU, 3), e.g. green, red, blue and white colour emission, each colour corresponding to a certain state or condition of the dose control system.

In yet a further embodiment, the dose control system can also comprise an alarm (ALA, 13) system, in communication with the central processing unit (CPU, 3), which can be configured to emit an audible alarm, say, in the case of malfunction of the system, or in the case of a failed injection, or for any other suitable condition or event detected within the system.

Figure 2A:
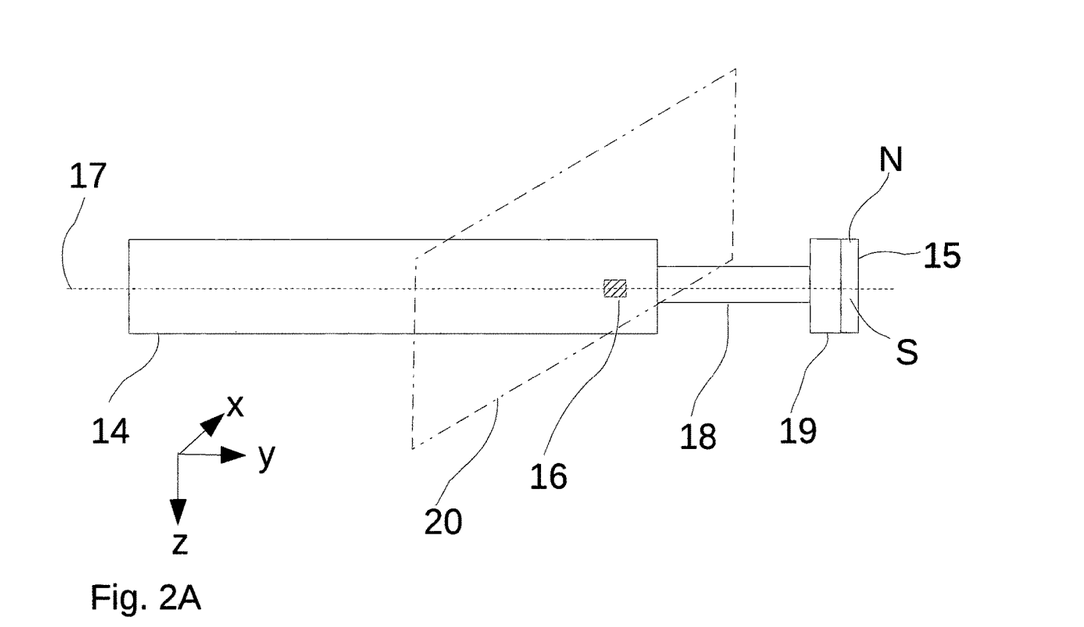
FIG. 2A is a schematic cross-sectional representation of a hypothetically ideal drug delivery device in which the magnetic field production means and the magnetic field measurement means are co-located along the longitudinal axis of the drug delivery device body, which in this representation is the Y axis.

FIG. 2A is a schematic representation of a hypothetically ideal drug delivery device having a drug delivery body 14 in which the magnetic field production means 15 and the magnetic field measurement means 16 are co-located along the longitudinal axis 17 of the drug delivery device body, which in this representation is the Y axis. Also shown in this figure are the north N and south S poles of a substantially disk-shaped diametral single-dipole magnet 15. The magnetic field measurement means 16, for example, a magnetometer, is located within the body 14 of the device, close to, and in axial alignment with, the longitudinal axis 17. The device also has a drive rod 18, and a dose selector wheel 19 connected to the drive rod which can rotate about the longitudinal axis 17 and translate along said axis. Magnet 15 is attached to the dose selector wheel 19, so that it too can rotate around the longitudinal axis. The rhomboid-shaped dotted line seen cutting through the body 14 of the device in line with the magnetometer 16 represents the plane in which measurements of magnetic field are made.

Figure 2B:
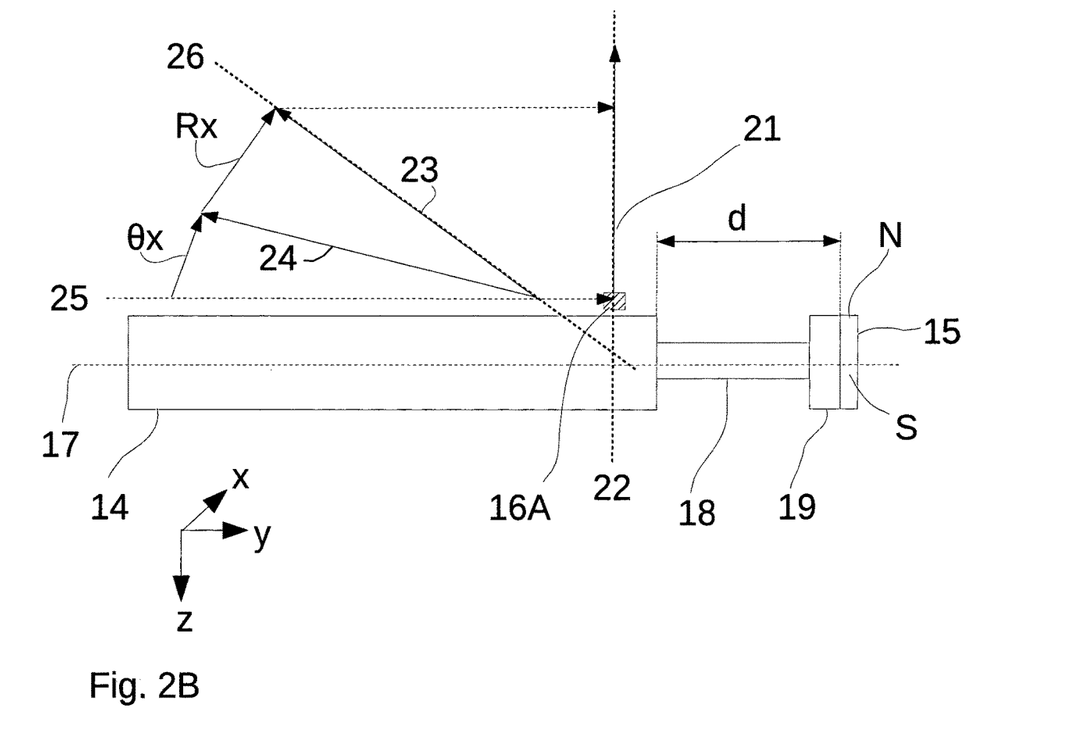
FIG. 2B is a similar schematic cross-sectional representation to FIG. 2A, the main differences however being that this schema represents a real-world system according to the invention, in which the magnetic field measurement means is located in a displaced axial alignment relative to the magnetic field production means and the longitudinal axis of the drug delivery device body.

FIG. 2B is a similar schematic representation to. FIG. 2A, the main differences however being that this schema represents a real-world system, in which the magnetic field measurement means is located distant from, and in non-axial alignment to the axis of the magnetic field production means, yet parallel thereto and the longitudinal axis of the drug delivery device body. In this schematic representation, only a single magnetometer 16A is represented to facilitate understanding. One can also see, in addition to the various elements already identified in FIG. 2A, several dashed lines and arrows representing the various magnetic fields, both measured and calculated, and the corresponding iso-normal projections. The arrow referenced 21 is the projection of the measured magnetic field vector onto the iso-normal plane 22. The arrow referenced 24 corresponds to the measured magnetic field vector and arrow referenced 23 corresponds to the pseudo-magnetic field vector calculated, by rotation of the magnetic fields 24 and 21 after projection, i.e. correction, to project it onto the iso-normal projection plane 26. The angle $R_x$, given in degrees, is the angle applied to transform the resultant magnetic field vector CR by rotation around the X axis in order to reposition it so that it is coplanar with its iso-normal projection plane 26. The angle, $\Theta_x$, is also indicated on FIG. 2B, and represents the angle, expressed in degrees, of the magnetic field, measured about the X axis.

As mentioned above, and repeated here for better understanding FIG. 2A, for each distance d, a plane exists that passes through the X axis, such that the projection of magnetic fields which are coplanar with said plane, along the plane XZ, are all equi-normal, irrespectively and independently of the angle of rotation of the magnet. This plane is known as the iso-normal projection plane. This calculation can be expressed as follows:

$R_x$ is an angle, indicated in degrees, enabling transformation of a magnetic field pseudo-vector by rotation around an orthogonal axis, preferably the X axis, to position said magnetic field vector, such that said pseudo-vector becomes substantially co-planar with its iso-normal projection plane.

$\Theta_x$ is the actual measured angle of rotation, in degrees, about the X axis, whereby:

$$\theta_x = a\tan\left(\frac{CR_z}{CR_y}\right)$$

and $$R_x = \frac{\log\frac{1}{\theta_x + c_2} - c_1}{c_3} xc_4 + c_5$$

In the above formula, $c_1$ to $c_5$ are constants which are calculated for each system and which take into account, and among others:
- the relative spatial locations of said first magnetometer ($m_1$) and said second magnetometer ($m_2$);
- the physical characteristics of said first and second magnetometers;
- the magnetic field producing capacity of the substantially disk-shaped diametral single-dipole magnet;
- the size of the substantially disk-shaped diametral single-dipole magnet;
- distance d
- and other optional parameters as deemed appropriate.

Factors or constants $c_1$ to $c_5$ can be determined as follows:
- a data set is generated for a representative subset of values of magnetic field. The data is generated for a representative variety of distances d. A simulation software program or library suitable for use in such simulated data generation, is that made available by Infineon, and known as the "3D Magnetic Sensor Design Tool", accessible via the following web page URL: http://design.infineon.com/3dsim/#/
- $R_x$ is approximated as a function of $\Theta_x$ for each simulation, whereby the difference between the normals of each projected magnetic field vector is minimized relative to the iso-normal projection;
- $R_x$ is modelled for values of $\Theta_x$ for each distance d leading to a set of values $d_i$, $\Theta_{xi}$ and $R_{xi}$, the values given below being merely illustrative for purposes of an example in relation to one particular system.

The following sample data values for the above model, for $R_x$ and $\Theta_x$ can be used:

| d | $\theta_x$ | $R_x$ |
|---|---|---|
| 0 | −12.21 | 35.15 |
| 2.8398 | −5.3 | 37.8 |
| 12.3058 | 12.12 | 45.07 |
| 17.0388 | 18.59 | 47.93 |
| 21.7718 | 24.07 | 50.55 |
| 31.2378 | 32.56 | 54.72 | where $R_x$ can be modelled as follows:

$$R_x = \frac{\log\frac{1}{\theta_x + V_{adjust}} - p_1}{p_2 - p_1} * (p_4 - p_3) + p_3$$

where:

$$p_1 = \min\left(\log\frac{1}{\theta_{xi} + V_{adjust}}\right)$$

$$p_2 = \max\left(\log\frac{1}{\theta_{xi} + V_{adjust}}\right)$$

$$p_3 = \max(R_{xi} - \theta_{xi})$$

$$p_4 = \min(R_{xi} - \theta_{xi})$$

$V_{adjust}$ is an adjustment variable for minimizing error between approximated values of $R_x$ obtained via simulation and the values of $R_x$ calculated by the system.

From the above, the following attributions can be made for the factors $c_1$ to $c_5$:

$c_1 = p_1$
$c_2 = V_{adjust}$
$c_3 = p_2 - p_1$
$c_4 = p_4 - p_3$
$c_5 = p_3$

Suitable example values of $c_1$ to $c_5$ for use in the system according to the invention can be:

$c_1 = -2.31864756900365$
$c_2 = 175.72$
$c_3 = 0.105103250465988$
$c_4 = 25.2$
$c_5 = 22.16$

Figure 3:
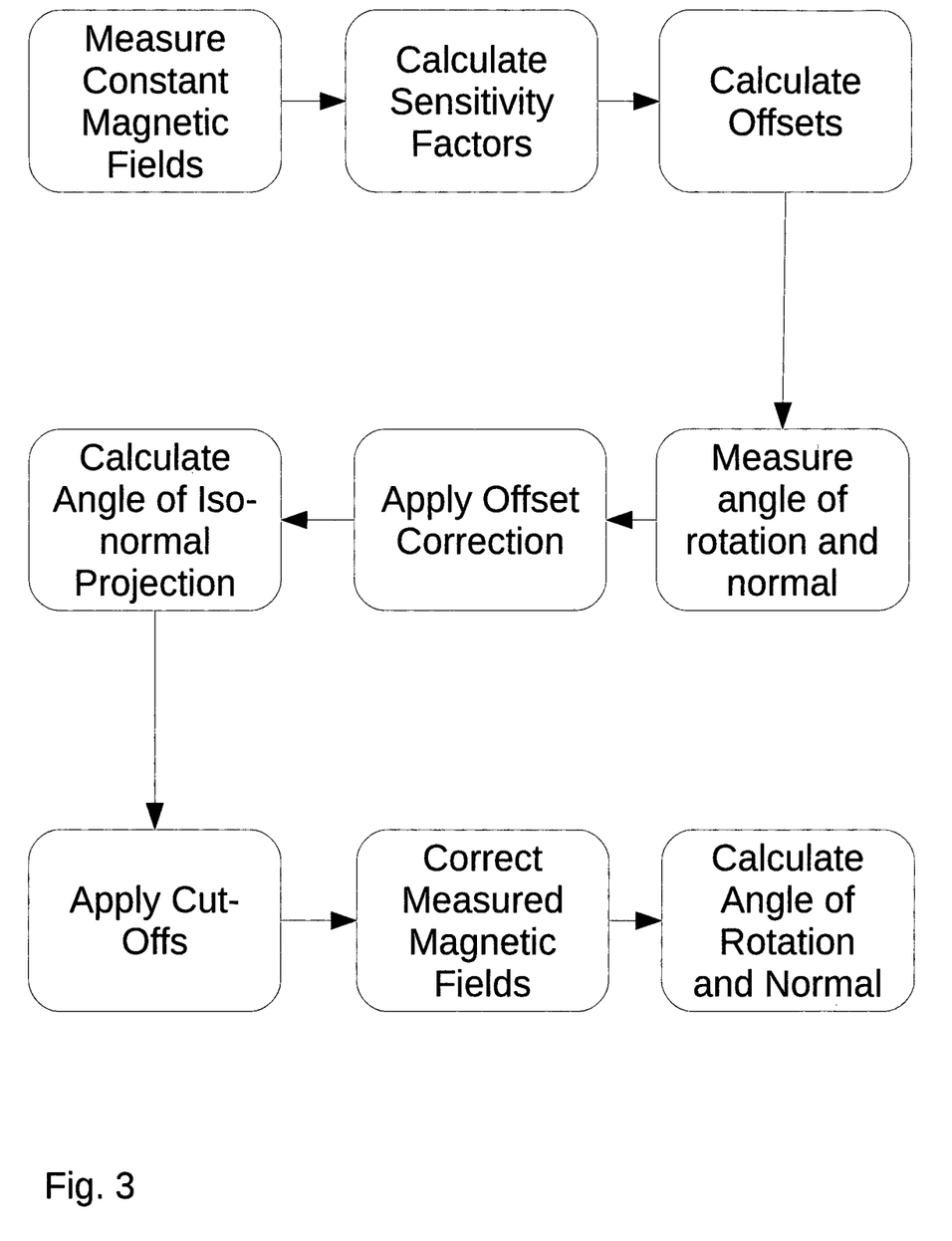
FIG. 3 is a schematic representation of a flow chart of the method or steps used to calculate a corrected angle of rotation in accordance with the present invention.

FIG. 3 is a schematic flow chart of one preferred method in which the system according to the invention can be set up and used, in other words, a method for calculating a dose setting which corresponds to a corrected magnetic field vector. In three initially optional steps, the magnetic field measurement means, in this example magnetometers m1 and m2, are first initialized by subjecting them to a constant magnetic field in all directions along all three orthogonal axes x, y and z to produce an array of measured reference values for each magnetometer:

$$\begin{bmatrix} m1_x \\ m1_y \\ m1_z \end{bmatrix} \text{ and } \begin{bmatrix} m2_x \\ m2_y \\ m2_z \end{bmatrix}$$

Then, the offset, or sensitivity, factors are calculated for each measurement, giving:

$$\begin{bmatrix} m1_{fx} \\ m1_{fy} \\ m1_{fz} \end{bmatrix} \text{ and } \begin{bmatrix} m2_{fx} \\ m2_{fy} \\ m2_{fz} \end{bmatrix}$$

These offset factors are then used to calculate the offsets for the measured magnetic values:

$$\begin{bmatrix} \text{Offset}_{m1x} \\ \text{Offset}_{m1y} \\ \text{Offset}_{m1z} \end{bmatrix} = \begin{bmatrix} \frac{(\max(m_{1fx} \cdot m_{1x_i}) + \min(m_{1fx} \cdot m_{1x_i}))}{2} \\ \frac{(\max(m_{1fy} \cdot m_{1y_i}) + \min(m_{1fy} \cdot m_{1y_i}))}{2} \\ \frac{(\max(m_{1fz} \cdot m_{1z_i}) + \min(m_{1fz} \cdot m_{1z_i}))}{2} \end{bmatrix}$$

and $$\begin{bmatrix} \text{Offset}_{m2x} \\ \text{Offset}_{m2y} \\ \text{Offset}_{m2z} \end{bmatrix} = \begin{bmatrix} \frac{(\max(m_{2fx} \cdot m_{2x_i}) + \min(m_{2fx} \cdot m_{2x_i}))}{2} \\ \frac{(\max(m_{2fy} \cdot m_{2y_i}) + \min(m_{2fy} \cdot m_{2y_i}))}{2} \\ \frac{(\max(m_{2fz} \cdot m_{2z_i}) + \min(m_{2fz} \cdot m_{2z_i}))}{2} \end{bmatrix}$$

These offset values are stored in the system, for example in the memory storage connected to the integrated processing unit, or within the integrated processing unit registers. It is even possible, with the appropriate magnetometers, to make the magnetic field offset calculation step optional as such magnetometers can be factory configured to take into account such a calculation.

When the dose control system is activated, the magnet is rotated and/or translated, and in so doing generates a magnetic field, the coordinate values of which in a three-dimensional space are measured by the first and second magnetometers m1 and m2 to give, as above, value arrays:

$$\begin{bmatrix} m1_x \\ m1_y \\ m1_z \end{bmatrix} \text{ and } \begin{bmatrix} m2_x \\ m2_y \\ m2_z \end{bmatrix}$$

The values which are measured for m1 and m2 can optionally be corrected by including the offset values generated previously and by taking into account the spatial orientation of the magnetometers:

$CR_x = -(m1_x * m1_{fx} - \text{Offset}_{m1x}) - (m2_x * m2_{fx} - \text{Offset}_{m2x})$ $CR_y = (m1_y * m1_{fy} - \text{Offset}_{m1y}) - (m2_y * m2_{fy} - \text{Offset}_{m2y})$ $CR_z = -(m1_z * m1_{fz} - \text{Offset}_{m1z}) - (m2_z * m2_{fz} - \text{Offset}_{m2z})$ Next, the iso-normal angle of projection is calculated using:

$$\theta_x = a\tan\left(\frac{CR_z}{CR_y}\right)$$

and:

$$R_x = \frac{\log\frac{1}{\theta_x + c_2} - c_1}{c_3} * c_4 + c_5$$

An optional cut off calculation step can also be included in the method, as illustrated in FIG. 3, to avoid reading errors based on the use of the arctangent functions a tan and a tan 2, especially when values close to the axes x, y and z are read. To this end, and in order to avoid amplifying any such errors through the calculations, $R_x$ is cut off at a lower limit and a higher limit, respectively $RX_{low}$ and $RX_{high}$. Such cut-off values can preferably be obtained via the functions $\min(\ominus x)$ and $\max(\ominus x)$ respectively, at the operating limits of the functioning system.

In order to bring the magnetic field pseudo-vector CR within the iso-normal projection plane of projection, it is rotated about the X axis to produce CR2 in the following manner:

$$\begin{bmatrix} CR2_x \\ CR2_y \\ CR2_z \end{bmatrix} = \begin{bmatrix} CR_x \\ CR_y \\ CR_z \end{bmatrix} * \begin{bmatrix} 1 & 0 & 0 \\ 0 & \cos R_x & -\sin R_x \\ 0 & \sin R_x & \cos Rx \end{bmatrix}$$

The values of CR2 are then used to calculate the angle of rotation of the magnet, and incidentally, the normal, by projection onto the XZ plane as follows:

$$\text{angle} = a\tan2\left(\frac{CR2_x}{CR2_z}\right)$$

which can then be used to calculate the normal in the following manner:

$$\text{normal} = \sqrt{CR2_x^2 + CR2_z^2}$$

Such a calculation therefore also allows for determination of precise position along the longitudinal axis of the drug delivery device should such information be appropriate or necessary for the operation of the device.

The invention claimed is:

1. A dose control system configured for an injectable drug delivery device, the drug delivery device comprising a substantially elongate drug delivery body, at least one injectable drug held by the body, the body having a distal and proximal extremity, and a rotatable dose setting wheel located at a proximal extremity of said drug delivery body, rotatable about a longitudinal axis of said drug delivery body, wherein the dose control system comprises:

a substantially disk-shaped diametral single-dipole magnet removably attachable, or permanently fixed, to the rotatable dose setting wheel at the proximal extremity of said drug delivery body;

a housing removably attachable to the proximal extremity of the drug delivery body, the removably attachable housing comprising:

at least a first and a second magnetic field measurement means configured to measure the magnetic field produced by the substantially disk-shaped diametral single-dipole magnet, wherein the at least first and second magnetic field measurement means are magnetometers, wherein the magnetometers are disposed in displaced axial alignment to an axis of rotation of the magnet;

an integrated control unit connected to the at least first and second magnetic field measurement means configured to process information received from the at least first and second magnetic field measurement means;

an integrated processing unit configured to correct magnetic field values measured by the at least first and second magnetic field measurement means and resulting from a lack of axial alignment of the at least first and second magnetic field measurement means with the substantially disk-shaped diametral single-dipole magnet by applying a rotation about the axis of rotation to a pseudo-vector representing a resultant pseudo-magnetic field calculated from the measured magnetic fields of said first and second magnetic field measurement means to bring said pseudo-vector into an iso-normal projection plane, wherein the at least first and second magnetic field measurement means are configured to measure the magnetic field produced by the substantially disk-shaped diametral single-dipole magnet via determination of a rotational movement of the substantially disk-shaped diametral single-dipole magnet and without determination of an axial position of the substantially disk-shaped diametral single-dipole magnet; wherein:

the at least first and second magnetic field measurement means are located in the removably attachable housing in a displaced axial relationship relative to the longitudinal axis of the drug delivery body and the substantially disk-shaped diametral single-dipole magnet;

the substantially disk-shaped diametral single-dipole magnet is configured to co-rotate with said dose setting wheel around the longitudinal axis of the drug delivery body; and the integrated control unit is further configured to:

calculate offset values for said at least first and second magnetic field measurement means from a series of points generated by corresponding vectors of the measured magnetic fields resembling a sphericized cloud of points in three dimensions, provide a normalized vector with regard to the displaced axial relationship of the at least first and second magnetic field measurement means, said normalized vector being derived from the measured magnetic field generated by the rotation of the substantially disk-shaped diametral single-dipole magnet and measured by the at least first and second magnetic field measurement means, and calculate a dose setting from said normalized vector.

2. The dose control system according to claim 1, wherein the integrated control unit is configured to calculate corrected offset values for said at least first and second magnetic field measurement means.

3. The dose control system according to claim 1, wherein the at least first and second magnetic field measurement means are located in the removably attachable housing adjacent to the proximal extremity of the drug delivery device body.

4. The dose control system according to claim 1, wherein the at least first and second magnetic field measurement means are located distally from the proximal extremity within said housing.

5. The dose control system according to claim 1, wherein the at least first and second magnetic field measurement means are located on a support structure located within the housing.

6. The dose control system according to claim 1, wherein the first magnetic field measurement means and the second magnetic field measurements are not in axial alignment with the substantially disk-shaped diametral single-dipole magnet.

7. The dose control system according to claim 1, wherein the first magnetometer and the second magnetometer are configured to simultaneously and independently measure the magnetic field produced as the substantially disk-shaped diametral single-dipole magnet is rotated about the longitudinal axis of the drug delivery device body.

8. The dose control system according to claim 1, wherein the integrated control unit is further configured to calculate offset values for said at least first and second magnetic field measurement means via the formula:

$$\begin{bmatrix} x_{offset} \\ y_{offset} \\ z_{offset} \end{bmatrix} = \begin{bmatrix} \frac{(\max(f_x \cdot x_i) + \min(f_x \cdot x_i))}{2} \\ \frac{(\max(f_y \cdot y_i) + \min(f_y \cdot y_i))}{2} \\ \frac{(\max(f_z \cdot z_i) + \min(f_z \cdot z_i))}{2} \end{bmatrix}$$

where x, y and z are the three orthogonal axes of magnetic field, and:

$x_i$, $y_i$, and $z_i$ are a series of points generated by corresponding vectors of the measured magnetic fields resembling a cloud of points in three dimensions, said cloud of points being sphericized by the factors:

$$\begin{bmatrix} x_i \\ y_i \\ z_i \end{bmatrix} = \begin{bmatrix} f_x \cdot x_i \\ f_y \cdot y_i \\ f_Z \cdot z_i \end{bmatrix}.$$

9. The dose control system according to claim 8, wherein the integrated control unit is further configured to correct said offset values via the formula:

$$\begin{bmatrix} x_{corrected} \\ y_{corrected} \\ z_{corrected} \end{bmatrix} = \begin{bmatrix} f_x \cdot x_i - x_{offset} \\ f_y \cdot y_i - y_{offset} \\ f_z \cdot z_i - z_{offset} \end{bmatrix}.$$

10. The dose control system according to claim 1, wherein the integrated processing unit is further configured to correct magnetic field values measured by the at least first and second magnetic field measurement means as a function of the non-axial alignment of the at least first and second magnetic field measurement means relative to the substantially disk-shaped diametral single-dipole magnet.

11. The dose control system according to claim 1, wherein the integrated processing unit is configured to apply the rotation to the pseudo-vector representing the resultant pseudo-magnetic field calculated from the measured magnetic fields of said first and second magnetic field measurement means, around one of the three orthogonal axes x, y or z, to bring said pseudo-vector representing said resultant pseudo-magnetic field into the iso-normal projection plane through application of the following calculations:

$$\theta_x = a\tan\left(\frac{CR_z}{CR_y}\right)$$

and $$R_x = \frac{\log\frac{1}{\theta_x + c_2} - c_1}{c_3} * c_4 + c_5$$

where $R_x$ is an angle expressed in degrees, enabling transformation of a measured magnetic field by rotation around an orthogonal axis, preferably the X axis, to reposition said magnetic field, expressed as an angular vector, such that said vector becomes substantially co-planar with its iso-normal projection plane; and $\Theta_x$ is the actual measured angle of rotation, in degrees, about the X axis;

$c_1 = p_1$;

$c_2 = V_{adjust}$;

$c_3 = p_2 - p_1$;
$c_4 = p_4 - p_3$;
$c_5 = p_3$
and:
$R_x$ is modelled for values of Ox for each distance d leading to a set of values $d_i$, $\ominus_{xi}$ and $R_{xi}$, as follows:

$$R_x = \frac{\log\frac{1}{\theta_x + V_{adjust}} - p_1}{p_2 - p_1} * (p_4 - p_3) + p_3$$

where:

$$p_1 = \min\left(\log\frac{1}{\theta_{xi} + V_{adjust}}\right);$$

$$p_2 = \max\left(\log\frac{1}{\theta_{xi} + V_{adjust}}\right);$$

$$p_3 = \max(R_{xi} - \theta_{xi});$$

$$p_4 = \min(R_{xi} - \theta_{xi});$$

and $V_{adjust}$ is an adjustment variable for minimizing error between approximated values of $R_x$ obtained via simulation and the values of $R_x$ calculated by the system.

12. The dose control system according to claim 1, wherein the integrated processing unit is configured to apply a low and high cut-off value to limit $R_x$ values obtained during processing.

13. The dose control system according to claim 1, wherein said low and high cut-off values are obtained via the functions min(⊕x) and max(⊕x) respectively, at the operating limits of the functioning system.

14. The dose control system according to claim 1, wherein said system further comprises a communication means configured to enable communication of information from the integrated control unit with a remote and/or local data processing system.

15. The dose control system according to claim 14, wherein the remote and/or local data processing system comprises a smartphone application.

16. The dose control system according to claim 1, wherein said dose control system further comprises a unique identifier that is communicated to a remote and/or local data processing system.

17. The dose control system according to claim 1, wherein said dose control system further comprises a temperature detection means.

18. The dose control system according to claim 1, wherein said dose control system further comprises a time determination means.

19. The dose control system according to claim 1, wherein said dose control system further comprises an autonomous power supply means.

20. The dose control system according to claim 1, wherein said dose control system is configured to permit an unhindered or unchanged modus operandi of said drug delivery system when compared to an off the shelf injectable-drug delivery device.

21. The dose control system according to claim 1, wherein a field strength of the magnet and a positioning of the first and second magnetic field measurement means are configured in such a way that a difference of at least 100 micro Tesla (µT) is present between the values measured at the first magnetic field measurement means and the second magnetic field measurement means.

22. The dose control system according to claim 1, wherein the rotatable dose setting wheel is not configured to translate in a longitudinal direction.

* * * * *